United States Patent
Brinker et al.

(10) Patent No.: US 6,172,004 B1
(45) Date of Patent: *Jan. 9, 2001

(54) COMPOSITION AND METHOD FOR TREATING PLANTS WITH EXOGENOUS CHEMICALS

(75) Inventors: Ronald J. Brinker, Ellisville; Jane L. Gillespie, St. Louis; Peter J. Raymond, Wildwood; Joseph J. Sandbrink, Des Peres; James M. Warner, Webster Groves; Al S. Wideman; Daniel R. Wright, both of St. Louis, all of MO (US)

(73) Assignee: Monsanto Company, St. Louis, MO (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/016,101

(22) Filed: Jan. 30, 1998

Related U.S. Application Data

(60) Provisional application No. 60/034,887, filed on Jan. 31, 1997, now abandoned.

(51) Int. Cl.$^7$ ............................. A01N 35/06; A01N 57/02
(52) U.S. Cl. ............................................ 504/127; 504/206
(58) Field of Search .................................. 504/118, 127, 504/206

(56) References Cited

U.S. PATENT DOCUMENTS

| | | | |
|---|---|---|---|
| 4,436,547 | 3/1984 | Sampson | 71/76 |
| 4,445,927 | 5/1984 | Gimesi et al. | 71/86 |
| 5,356,861 | 10/1994 | Gednalski et al. | 504/206 |
| 5,817,600 | 10/1998 | Carstairs et al. | 504/115 |
| 5,834,006 | 11/1998 | Smith et al. | 424/409 |

FOREIGN PATENT DOCUMENTS

| | | | |
|---|---|---|---|
| 0 036 106 | 9/1981 | (EP) . | |
| 0 134 198 | 3/1985 | (EP) . | |
| 0 243 522 | 11/1987 | (EP) . | |
| 0 390 743 | 10/1990 | (EP) . | |
| 2 119 860 | 8/1972 | (FR) . | |
| 2 124 092 | 9/1972 | (FR) . | |
| 2 131 819 | 11/1972 | (FR) . | |
| 2 168 186 | 8/1973 | (FR) . | |
| 89/03176 | 4/1989 | (WO) . | |
| 94/27444 | 12/1994 | (WO) | A01N/63/02 |

OTHER PUBLICATIONS

The Agrochemicals Handbook. "anthraquinone", Aug. 1981.
Basler, Eddie and McBride, Rebecca, "Effects of Coumarin, Juglone and Abscisic Acid on the Translocation of Auxin," Proceedings of the Plant Growth Regulator Working Group, vol. 4, 1977, pp. 295–300.
Chykaliuk, Peter et al., "Effects of the Growth Regulator GAF 141 on the Downward Translocation of Herbicides," Proceedings of the Plant Growth Regulator Working Group, vol. 7, 1980, pp. 3–28.
Chykaliuk, Peter et al., "Stimulation of Basipetal Herbicide Translocation with GAF 141," Weed Science, 1982, 30:6–10.
Research Disclsoure (No. 139): pp. 7–8 (1975) "Herbicidal mixtures," 00456806 CAB Accession Number: 762312291.
Turner, D. J. and Loader, M. P.C., "Effect of ammonium sulphate and other additives upon the phytotoxicity of glyphosate to *Agropyron repens* (L.) Beauv," *Weed Research*, 1980, 20: 139–46.

*Primary Examiner*—S. Mark Clardy
(74) *Attorney, Agent, or Firm*—James C. Forbes; Arnold White & Durkee

(57) ABSTRACT

Compositions of exogenous chemicals, particularly phloem-mobile exogenous chemicals, are provided for treatment of plants, wherein the composition comprises the exogenous chemical and an enhancing agent consisting of an anthraquinone or substituted anthraquinone. Specific compositions contain herbicides, particularly N-phosphonomethylglycine and herbicidal derivatives thereof, i.e., glyphosate. The compositions exhibit enhanced effectiveness compared to compositions in which the enhancing agent is not present. Also provided are processes for applying an exogenous chemical with an anthraquinone or substituted anthraquinone enhancing agent to achieve enhanced biological effectiveness.

40 Claims, No Drawings

COMPOSITION AND METHOD FOR TREATING PLANTS WITH EXOGENOUS CHEMICALS

This application claims the benefit of provisional application Ser. No. 60/034,887 filed Jan. 31, 1997, now abandoned, which is incorporated herein by reference.

BACKGROUND OF THE INVENTION

The present invention relates to a process for enhancing the reliability and consistency of biological effectiveness of an exogenous chemical substance applied to foliage of a plant. The process involves application of a compound from the anthraquinone and substituted anthraquinone family (herein referred to as anthraquinone compounds) to the foliage, either sequentially or simultaneously with the exogenous chemical substance. The invention also relates to plant treatment compositions comprising an exogenous chemical substance and an anthraquinone compound.

For many purposes in agriculture and related endeavors it is desired to treat plants with exogenous chemical substances of various kinds. An exogenous chemical substance as defined herein is a chemical substance, whether naturally or synthetically obtained, which is applied to a plant with the intent or result of delivering the substance to one or more sites in the plant where the substance expresses some desired biological activity. Examples of exogenous chemical substances include, but are not limited to, chemical pesticides (such as herbicides, algicides, fungicides, bactericides, viricides, insecticides, miticides, nematicides and molluscicides), plant growth regulators, fertilizers and nutrients, gametocides, defoliants, desiccants, mixtures thereof and the like.

Many exogenous chemical substances are applied to foliage (ie. leaves and other non-woody above-ground parts) of a plant, and have a site of action in the plant either close to or remote from the locus of application. Such substances are referred to herein as foliar-applied exogenous chemical substances. Typically, by plant treatment methods known in the art, only a small portion of the amount of an exogenous chemical substance applied to foliage reaches sites of action in the plant where the biological effect of the exogenous chemical substance can be usefully expressed. It is therefore a major desideratum in agriculture and related endeavors to enhance the efficiency of delivery of foliar-applied exogenous chemical substances to their sites of action in plants, and thereby to enhance the biological effectiveness of the exogenous chemical substance for the purpose for which it is used.

Application to foliage of an exogenous chemical substance by methods known in the art does not universally result in inefficient delivery to sites of action. In some situations such methods provide excellent biological effectiveness, even at low use rates of the exogenous chemical substance. The problem is that it is seldom possible to identify those situations in advance, partly because so many factors influence delivery efficiency. These factors include weather (temperature, relative humidity, daylength, cloudiness, precipitation, wind, etc.) preceding, during and following application, soil conditions (fertility, aeration, etc.), plant growth stage, health and physiological status, equipment-related inaccuracies in application, and other factors. Therefore, to help ensure reliable and consistent biological effectiveness of a foliar-applied exogenous chemical substance, the user typically applies the substance at a higher rate than truly necessary in the majority of situations.

Benefits of a method giving greater reliability include an ability to reduce rates of application of exogenous chemical substances without sacrificing consistency of biological effectiveness. Pressures felt by the agricultural industry to reduce pesticide, particularly herbicide, usage are well evidenced by symposia on the subject, such as that held in 1993 by the Weed Science Society of America and documented in Weed Technology 8, 331–386 (1994). Reduced use rates bring rewards not only environmentally but also economically, as the cost per unit area treated decreases.

Herbicidal compositions have been described containing chemical synergists which have been hypothesized to enhance herbicidal effectiveness by affecting metabolic processes of the plant. Such chemical synergists have included 6-benzylaminopurine, gibberellic acids, and 2-choroethylphosphonic acid, all known to have plant growth regulating activity in their own right. For example, some researchers have reported that if gibberellic acids are applied to growing plants at some time prior to the application of a glyphosate herbicide composition, the herbicidal effectiveness of the glyphosate is increased. However, the use of some synergists such as 6-benzylaminopurine, gibberellic acids, and 2-choroethylphosphonic acid is limited because of the need to apply the synergist days or even weeks before the application of the herbicide. Other synergists, while capable of being applied simultaneously with the herbicide, are effective only at high concentrations, e.g., 1:1 or 2:1 ratios by weight of the exogenous chemical substance to synergist.

A widely practiced method of enhancing reliability of biological effectiveness of a foliar-applied composition of an exogenous chemical substances, particularly a herbicide, is to add an enhancing agent comprising an ammonium salt, most commonly ammonium sulfate, to the composition being applied. It is well known to those practicing this method that enhanced biological effectiveness is not assured with every use; however the low cost of the method means that even if biological effectiveness is enhanced in only a small proportion, for example 1 in 5, of times the method is used, it is still worthwhile.

There are limitations to the usefulness of ammonium salts as enhancing agents resulting from the relatively high rates that have to be used. Ammonium sulfate, for example, is typically used at concentrations in an aqueous application solution of 1–5% weight/volume, for example around 2% weight/volume. Common spraying equipment used in agriculture applies a spray volume of 50–1000 liters per hectare (1/ha) of solution; at a typical spray volume of 200 l/ha containing 2% ammonium sulfate, the use rate of ammonium sulfate is 4 kg/ha. Such a high use rate leads to inconvenience for the user and difficulties for the formulator desiring to provide a product combining both an exogenous chemical substance and an enhancing agent based on ammonium sulfate.

Most exogenous chemical substances are designed to be used at much lower rates than those shown above for ammonium sulfate, for example 1–1000 grams of active ingredient per hectare (g a.i./ha). Thus, in an application method using ammonium sulfate, the amount of ammonium sulfate used is typically much greater than the amount of the exogenous chemical substance. It is consequently uneconomic in most situations for the manufacturer of the exogenous chemical substance to supply a useful amount of ammonium sulfate preformulated with the exogenous chemical substance. Economics in the agricultural pesticide business, for example, mandate that the pesticide be formulated at as high a concentration or loading as possible to minimize packaging, shipping and storage costs. The requirement to coformulate a large amount of ammonium sulfate with the pesticide active ingredient is inconsistent with achieving a high loading of active ingredient.

It is therefore an objective of the present invention to provide an agent that enhances the reliability of effectiveness of foliar applied exogenous chemical substances but that achieves this at much lower use rates than is the case with ammonium sulfate.

Many studies have been conducted in pursuit of this elusive goal. As biological effectiveness of an exogenous chemical substance depends upon delivery of the substance into living cells or tissues of the plant, some investigators have focused the search for a low-rate enhancing agent on classes of compounds which, at low rates, can be expected to stimulate various biological processes in plants. U.S. Pat. No. 4,436,547 to Sampson discloses that additives to improve the action of agricultural chemicals can include a carbohydrate source or organic acid to supply metabolizable energy or as precursors of amino acids and nucleotides, a vitamin or coenzyme to stimulate metabolic processes, a nucleic acid precursor to stimulate nucleic acid synthesis, a fatty acid (or fat or oil that can be degraded thereto) as precursor of molecules required in growth processes, an amino acid as structural unit for protein synthesis, and a naturally occurring plant growth regulator to affect metabolism in such a way as to render an applied pesticide more effective. In the case of herbicides, it is postulated in the above cited patent that "by stimulating growth and uptake of applied chemicals it is possible to enhance the activity of a number of herbicides, especially against older more established weeds."

The present invention provides a process for enhancing biological effectiveness of a foliar-applied exogenous chemical substance involving an enhancing agent not contemplated by Sampson, namely an anthraquinone compound as herein defined.

SUMMARY OF THE INVENTION

A process for treating a plant with an exogenous chemical substance is provided, comprising the steps of (a) applying to foliage of the plant an anthraquinone compound more particularly defined below and (b) applying a biologically effective amount of the exogenous chemical substance to the same foliage, wherein the anthraquinone compound is in a substantially non-phytotoxic amount of at least about 0.25 g/ha but not suficient to antagonize biological effectiveness of the exogenous chemical substance.

For the purposes of the present invention, an anthraquinone compound is defined as a six-membered carbon ring having double bonded oxygen atoms attached to two carbon atoms in that ring, and two phenyl rings fused to the six-membered carbon ring, optionally containing one or more substitutions on one or more of the rings. Preferably the oxygen atoms are in the para- configuration, i.e. attached directly opposite each other on the six-membered carbon ring. One group of anthraquinone compounds has the formula:

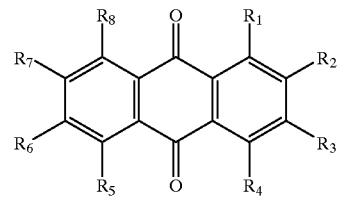

where $R_1$ through $R_8$ are independently hydrogen, alkyl groups having from 1 to 30 carbon atoms, alkenyl groups having from 2 to 30 carbon atoms, alkoxy groups having from 1 to 30 carbon atoms, halogen, amino groups, alkylamino groups having from 1 to 30 carbon atoms, hydroxy groups, hydroxyalkyl groups having from 1 to 30 carbon atoms, cyano groups, nitro groups, haloalxyl groups having from 1 to 30 carbon atoms, carboxy groups, and aryl groups having 1 to 30 carbon atoms such as but not limited to phenyl, morpholino, and pyrrolidino.

In one preferred embodiment of the invention, in the anthraquinone compound of formula I, $R_1$ is hydrogen, —$NH_2$, or —$NHCH_3$; $R_2$ is hydrogen, hydroxymethyl, methyl, or —$NH_2$; $R_5$ and $R_6$ are independently hydrogen or —$NH_2$; and $R_3$, $R_4$, $R_7$, and $R_8$ are hydrogen.

In a particularly preferred embodiment of the invention, in the anthraquinone compound of formula I, one or two of $R_1$, $R_2$, $R_3$, $R_4$, $R_5$, $R_6$, $R_7$, and $R_8$ are methyl, ethyl, hydroxymethyl, amnino, or methylamino, and all other R substituents are hydrogen.

Also included within the definition of anthraquinone compounds in this invention are compounds that will be converted in formulation or upon application to a plant into a compound having the structure defined above.

By "substantially non-phytotoxic" is meant that in the amount used herein the anthraquinone compound, if applied in the absence of the exogenous chemical substance, causes no significant injury, growth reduction, herbicidal effect or readily visible symptoms to the plant.

In the process of the present invention, application of the exogenous chemical substance and application of the anthraquinone compound occur either sequentially or simultaneously. In the case of simultaneous application, the exogenous chemical substance and the anthraquinone compound can be components of a single composition adapted for such application.

Thus an embodiment of the present invention is a plant treatment composition comprising (a) an exogenous chemical substance and (b) an anthraquinone compound as defined above, such that, when the composition is applied to foliage of a plant with or without prior dilution, dispersion or dissolution in an application medium, the exogenous chemical substance is in a biologically effective amount and the anthraquinone compound is in a substantially non-phytotoxic amount of at least about 0.25 g/ha but not sufficient to antagonize effectiveness of the exogenous chemical substance. Typically the application medium appropriate for compositions of the invention is water.

Anthraquinone compounds useful in the process and compositions of the present invention generally enhance reliability of effectiveness of foliar-applied exogenous chemical substances at rates much lower than rates typically required of ammonium sulfate. Preferred anthraquinone compounds are useful in the present process and compositions at rates up to about 250 g/ha.

The present invention has several benefits and advantages. One benefit is that the invention provides a process for treating plants with a foliar-applied exogenous chemical substance that enhances the reliability of effectiveness of the exogenous chemical substance. In addition, the present invention enhances the reliability of effectiveness of foliar-applied exogenous chemical substances in plants at very low use rates, for example from about 0.25 to about 250 g/ha, so that, among other advantages, it becomes economically feasible to include the agent in a concentrate composition without excessively reducing the loading therein of the exogenous chemical substance. A further benefit of the invention is provision of a composition containing an exogenous chemical substance that, through selection of an appropriate anthraquinone compound for inclusion in such composition, is better adapted for specific uses than existing compositions of the exogenous chemical substance.

DESCRIPTION OF SPECIFIC EMBODIMENTS

A nonlimiting list of anthraquinone compounds that can be employed in the present invention includes:

anthraquinone;
1-(methylamino)anthraquinone;
1-amino-4-bromo-2-methylanthraquinone;
1-aminoanthraquinone;
1-chloroanthraquinone;
1,2-dianoantaquinone;
1,4-diaminoanthraquinone;
1,5-diaminoanthraquinone;
1,8-dichloroanthraquinone;
1,8-dihydroxyanthraquinone;
2-(hydroxymethyl)anthraquinone;
2-aminoanthraquinone;
2-ethylanthraquinone;
2-methylanthraquinone;
2-tert-butylanthraquinone;
2,6-diaminoanthraquinone.

Also suitable for use in the present invention are compounds that will through some process such as hydrolysis be converted to an anthraquinone compound. The conversion could be due to some natural degradation process, contact with the foliage of the plant, exposure to the atmosphere, contact with the herbicide or other exogenous chemical, contact with some other coformulant, contact with some chemical previously or subsequently applied to the plant, incorporation into an aqueous solution, or some other means.

Anthraquinone compounds as described above surprisingly enhance reliability of effectiveness of exogenous chemical substances at rates much lower than rates typically required of ammonium sulfate. Preferred anthraquinone compounds are useful in the present method at rates up to about 250 g/ha and are themselves substantially non-phytotoxic at such rates.

A further embodiment of the invention is a plant treatment composition comprising an exogenous chemical substance and an anthraquinone compound having a chemical formula as defined above. The weight/weight ratio of anthraquinone compound to exogenous chemical substance in such a composition can vary within wide limits, subject to the following proviso: when the composition is applied at a rate appropriate to provide a biologically effective amount of the exogenous chemical substance, it is important that the amount of the anthraquinone compound provided by the composition be at least about 0.25 g/ha but not sufficient to antagonize effectiveness of the exogenous chemical substance. Preferably the weight/weight ratio of anthraquinone compound to exogenous chemical substance is such that when the composition is applied at a rate appropriate to provide an effective amount of the exogenous chemical substance, the anthraquinone compound is applied in a substantially non-phytotoxic amount from about 0.25 to about 250 g/ha.

Compositions of the invention can take the form of dilute ready-to-apply solutions or dispersions, referred to herein as spray compositions, as well as liquid and solid concentrates which, on dilution, dispersion or dissolution in water or other carrier, provide such spray compositions.

In making a liquid or solid concentrate, the exogenous chemical substance is typically blended by the manufacturer with suitable formulation ingredients. Such ingredients are well known to those of skill in the art and their selection depends on the exogenous chemical substance and on the use to which it will be put. They include, without limitation, solvents, surfactants, dispersants, thickening agents, antifoams, dyes, antifreezes, preservatives and the like. In an embodiment of the present invention, the process provided includes a step of adding an anthraquinone compound during the making of a concentrate composition of an exogenous chemical substance. This concentrate composition is later diluted, dissolved or dispersed in water to make a spray composition, which is then applied by spraying to the foliage of plants.

If both the exogenous chemical substance and the anthraquinone compound are readily soluble in water, a liquid concentrate can be provided as a simple aqueous solution. If, on the other hand, neither is readily soluble in water, various ways are known in the art of formulating them as liquid concentrates, including emulsifiable concentrates, suspension concentrates and aqueous emulsions.

Of particular interest are situations in which the exogenous chemical substance is readily water-soluble and the anthraquinone compound is oil-soluble. In such situations, a preferred form of concentrate composition of the invention is an emulsion having an aqueous phase and an oil phase, wherein the exogenous chemical substance is present primarily in the aqueous phase and the anthraquinone compound is present primarily in the oil phase, and wherein the emulsion is stabilized by means of one or more emulsifiers. The oil phase can comprise any of a large number of organic oils and solvents known in the agricultural chemical formulation art, including paraffinic and aromatic oils, or fatty acid alkylesters such as butyl stearate, isopropyl myristate or methyl oleate. Alternatively, the oil phase can consist essentially of the anthraquinone compound itself. Emulsion compositions of the invention include oil-in-water macroemulsions and microemulsions, water-in-oil or invert emulsions, and water-in-oil-in-water multiple emulsions.

While the invention is not limited to any particular class of foliar-applied exogenous chemical substance, it has been found to provide useful benefits for substances that rely at least in part for their biological effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected sympastically by plasmodesmata, or via both apoplastic and symplastic pathways. For foliar-applied systemic exogenous chemical substances, the most important pathway is the phloem, and the present invention is believed to provide the greatest benefits for exogenous chemical substances that are phloem-mobile.

The method has proved particularly useful as a herbicidal method, wherein the exogenous chemical substance is a foliar-applied herbicide, preferably a phloem-mobile foliar-applied herbicide. While it is likely that anthraquinone compounds have the greatest applicability where the exogenous chemical substance is systemic, anthraquinone compounds also enhance biological effectiveness of non-systemic exogenous chemical substances such as the herbicide paraquat.

Preferred systemic exogenous chemical substances are those which are water soluble, particularly those that exist in the form of a salt comprising a biologically active ion and a counterion which is biologically inert or relatively inactive. It is further preferred that such a salt has a molecular weight below about 300, excluding any counterions. Especially suitable among such low molecular weight salts are herbicides, plant growth regulators and nematicides, in particular those having an amine, a carboxylic acid, a phosphonate or a phosphinate functional group in the biologically active ion. Among the most preferred of such salts are those having an amine group, a carboxylic acid group, and either a phosphonate or phosphinate group in the biologically active ion. These include salts of glyphosate and salts of glufosinate.

Illustratively herbicides that can be used in the method of the invention include aminotriazole, asulam, bentazon, bialaphos, bipyridyls such as paraquat, bromacil, clopyralid, cyclohexenones such as sethoxydim, dicamba, diphenylethers such as acifluorfen, fomesafen and oxyfluorfen, fosamine, glufosinate, glyphosate, hydroxybenzonitriles such as bromoxynil, imidazolinones such as imazethapyr, isoxaben, phenoxies such as 2,4-D, phenoxypropionates such as quizalofop, picloram, substituted ureas such as fluometuron, sulfonylureas such as chlorimuron, chlorsulfaron, halosulfuron and sulfometuron, and triazines such as atrazine and metribuzin. Phloem-mobile herbicides that are preferred for use by the method of the invention include but are not limited to aminotriazole, asulam, bialaphos, clopyralid, cyclohexenones, dicamba, glufosinate, glyphosate, imidazolinones, phenoxies, phenoxypropionates, picloram and sulfonylureas.

Herbicidally active derivatives of the above herbicides and of other herbicides are also within the scope of the invention if applied by the method herein described. A herbicidally active derivative is any compound which is a minor structural modification, most commonly but not restrictively a salt or ester, of a herbicide, said compound retaining the essential activity of the parent herbicide although not necessarily having a potency equal to that of the parent herbicide. Usually but not always, the derivative converts to the parent herbicide before or after it enters the treated plant, and is analogous to a pro-drug that converts to an active drug in vivo. Mixtures or coformulations of a herbicide or herbicidally active derivative with other ingredients, or of more than one herbicide, are likewise within the scope contemplated by the present invention.

An especially preferred herbicide useful in the method and compositions of the present invention is glyphosate. The term "glyphosate" is used herein to refer collectively to the parent herbicide N-phosphonomethylglycine (otherwise known as glyphosate acid), to a salt or ester thereof, or to a compound which is converted to N-phosphonomethylglycine in plant tissues or which otherwise provides N-phosphonomethylglycine in ionic form (otherwise known as glyphosate ion). Illustratively, glyphosate salts useful herein are disclosed in U.S. Pat. Nos. 3,799,758 and No. 4,405,531 to Franz, the disclosure of which is incorporated herein by reference. Glyphosate salts that can be used according to the present invention include but are not restricted to alkali metal, for example sodium and potassium, salts; ammonium salt; alkylamine, for example dimethylamine and isopropylamine, salts; alkanolamine, for example monoethanolamine, salt; alkylsulfonium, for example trimethylsulfonium, salts; mixtures thereof and the like. The N-phosphonomethylglycine molecule has three acid sites having different pKa values; accordingly mono-, di- and tribasic salts, or any mixture thereof, or salts of any intermediate level of neutralization, can be used.

Glyphosate salts are commercially significant in part because they are water soluble. Many ammonium, alkylamine, alkanolamine, alkylsulfonium and alkali metal salts are highly water soluble, allowing for formulation as highly concentrated aqueous solutions which can be diluted in water at the point of use. The present invention encompasses compositions containing a glyphosate salt in aqueous solution, and further containing an appropriate amount of an anthraquinone compound, so that on dilution and application to plant foliage both glyphosate and the anthraquinone compound are deposited simultaneously on the foliage. As indicated above, the anthraquinone compound, if water-soluble, can be dissolved in the same aqueous solution as the glyphosate salt; however more commonly the anthraquinone compound is only sparingly water-soluble and is held in stable dispersion in the aqueous solution by means of one or more emulsifiers. If desired, a sparingly water-soluble anthraquinone compound can be dissolved in an oil or organic solvent which is then blended with one or more emulsifiers and an aqueous solution of glyphosate salt to form a stable emulsion having glyphosate primarily in the aqueous phase and the anthraquinone compound primarily in the oil phase.

Glyphosate concentrates of the invention, whether aqueous solutions or emulsions, can contain from about 50 to about 500 grams per liter of glyphosate, expressed as acid equivalent (g a.e./l). Higher glyphosate concentrations, for example from about 300 to about 500 g a.e./l, are preferred.

Glyphosate salts are alternatively formulated as water soluble or water dispersible compositions, in the form for example of powders, granules, pellets or tablets. Such compositions are often known as dry formulations, although the term "dry" should not be understood in this context to imply the complete absence of water. Typically, dry formulations contain less than about 5% by weight of water, for example from about 0.5% to about 2% by weight of water. Such formulations are intended for dissolution or dispersion in water at the point of use. The present invention encompasses water soluble or water dispersible dry formulations containing, in addition to a glyphosate salt, an appropriate amount of an anthraquinone compound, so that on application to plant foliage both glyphosate and the anthraquinone compound are deposited simultaneously on the foliage. Even if an emulsifier is not necessary to make a stable dry glyphosate formulation containing a sparingly water-soluble anthraquinone compound, it is preferred to include one or more emulsifiers in the formulation to enhance dispersion and stability of the spray composition formed when the dry formulation is added to water. Contemplated dry glyphosate formulations can contain from about 5% to about 80% by weight of glyphosate, expressed as acid equivalent (% a.e.). Higher glyphosate concentrations within the above range, for example from about 50% to about 80% a.e., are preferred.

Liquid and dry concentrate formulations of the invention can optionally contain, in addition to an exogenous chemical substance and an anthraquinone compound, any other desired ingredients. Especially useful ingredients, at least in the case of glyphosate compositions, are surfactants, which assist in retention of aqueous spray solutions on the relatively hydrophobic surfaces of plant leaves, as well as helping the glyphosate, and perhaps the anthraquinone compound, to penetrate the waxy outer layer (cuticle) of the leaf and thereby contact living tissues within the leaf. Surfactants can perform other useful functions as well, including serving as emulsifiers to permit the anthraquinone compound to be incorporated in a stable homogeneous formulation, as indicated above.

There is no restriction in the type or chemical class of surfactant that can be used in compositions of the invention. Nonionic, anionic, cationic and amphoteric types, or combinations of more than one of these types, are all usefuil in particular situations. For glyphosate compositions, however, it is generally preferred that at least one of the surfactants, if any, present should be other than anionic.

Among nonionic surfactants, especially preferred classes include polyoxyalkylene alkyl and alkylaryl ethers, such as ethoxylated primary or secondary alcohols or alkylphenols, polyoxyalkylene alkyl esters, such as ethoxylated fatty acids, polyoxyalkylene sorbitan alkyl esters, glyceryl alkyl esters, sucrose esters, alkyl polyglycosides, and the like.

Among cationic surfactants, especially preferred classes include polyoxyalkylene tertiary alkylamines, such as ethoxylated fatty amines, quaternary ammonium surfactants, polyoxyalkylene alkyletheramines, and the like. Particularly preferred polyoxyalkylene alkyletheramines are those disclosed in PCT Publication No. WO 96/32839.

Among amphoteric surfactants, especially preferred classes include polyoxyalkylene alkylamine oxides, alkylbetaines, alkyl-substituted amino acids and the like.

Hydrophobic moieties of surfactants useful in compositions of the invention can be essentially hydrocarbon based, or can contain silicon atoms, for example in the form of siloxane groups, or fluorine atoms, for example as partially fluorinated alkyl or perfluoroalkyl groups. Hydrocarbon chains of surfactants useful herein typically have from about 8 to about 20, preferably from about 12 to about 18, carbon atoms, and are branched or unbranched, saturated or unsaturated. Polyoxyalkylene moieties of surfactants useful in compositions of the invention are preferably polyoxyethylene or polyoxyethylene-polyoxypropylene chains.

Standard reference sources from which one of skill in the art can select suitable surfactants, without limitation to the above mentioned classes, include Handbook of Industrial Surfactants, Second Edition (1997) published by Gower, McCutcheon's Emulsifiers and Detergents, North American and International Editions (1997) published by MC Publishing Company, and International Cosmetic Ingredient Dictionary, Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

As an alternative to providing the anthraquinone compound as a component of the exogenous chemical formulation, it can be provided in a separate composition. In such a case the composition comprising the anthraquinone compound is typically tank-mixed with the exogenous chemical substance. A tank-mixed composition is prepared by the user as a single spray composition by dilution, dissolution or dispersion in water of two concentrate compositions, one containing the exogenous chemical substance and the other containing the anthraquinone compound. The two concentrate compositions can be supplied independently or in a twin-pack or other form of combined packaging. A particular embodiment of the invention is a concentrate composition comprising an anthraquinone compound together with one or more surfactants; this composition being useful as an adjuvant for tank-mixing with an exogenous chemical substance prior to application to plant foliage. Where the composition is to be used as an adjuvant to glyphosate, it is preferred that at least one surfactant, if any, in the composition should other than anionic. Preferred classes of surfactant are as listed above.

An anthraquinone compound, or composition thereof, can illustratively be used according to a method provided herein in tank-mixture with any commercial formulation of glyphosate. Examples of such formulations include, without restriction, those sold by Monsanto Company as ROUNDUP®, ROUNDUP® ULTRA, ROUNDUP® CT, ROUNDUP® BIACTIVE, ROUNDUP® BIOFORCE, RODEO®, POLARIS®, SPARK® and ACCORD® herbicides, all of which contain glyphosate as its isopropylamine salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

Alternatively, an anthraquinone compound, or composition thereof, can illustratively be used according to the method provided herein as a pre-treatment or post-treatment before or after foliar application of any commercial formulation of glyphosate including, without restriction, those exemplified above. When an anthraquinone compound is applied to foliage as a pre-treatment or post-treatment, the interval between this treatment and application of the glyphosate or other exogenous chemical substance should be such as to allow the anthraquinone compound to enhance reliability of effectiveness of the exogenous chemical substance. Such an interval is described herein as an "effective time period". What constitutes an effective time period varies depending on species of plant, on the particular exogenous chemical substance and on the particular anthraquinone compound, among other factors. In the case of glyphosate, for example, an interval of from 0 to about 96 hours can be an effective time period, but preferably the interval is from 0 to about 24 hours. Where sequential application is employed, a preferred sequence is for the anthraquinone compound to be applied before the exogenous chemical substance. An optimum interval can readily be determined for any combination of exogenous chemical substance, anthraquinone compound and plant species by preliminary tests.

The selection of application rates for a specific exogenous chemical substance that are biologically effective is also within the skill of the ordinary agricultural technician. One of skill in the art will likewise recognize that individual plant conditions, weather and growing conditions, as well as the specific exogenous chemical substance selected, can affect the results achieved in practicing the method of the present invention. Where the exogenous chemical substance is glyphosate, much information is available in published literature about appropriate application rates. Over two decades of glyphosate use and published studies relating to such use have provided abundant information from which a weed control practitioner can select glyphosate application rates that are herbicidally effective on particular species at particular growth stages in particular environmental conditions.

The method of the present invention where the exogenous chemical substance is glyphosate, more particularly a water-soluble glyphosate salt, is applicable to any and all plant species on which glyphosate is biologically effective as a herbicide or plant growth regulator. This encompasses a very wide variety of plant species worldwide. Likewise, compositions of the invention containing glyphosate can be applied to any and all plant species on which glyphosate is biologically effective.

For example, where the exogenous chemical substance is glyphosate, annual broadleaf species on which the method and compositions of the invention can be employed include, without limitation, Abutilon theophrasti (velvetleaf), Amaranthus spp. (pigweed), Borreria spp. (buttonweed), Brassica spp. (oilseed rape, canola, indian mustard, etc.), Commelina spp. (commelina), Erodium spp. (filaree), Helianthus spp. (sunflower), Ipomoea spp. (morningglory), Kochia scoparia (kochia), Malva spp. (mallow), Polygonum spp. (wild buckwheat, smartweed, etc.), Portulaca spp. (purslane), Salsola spp. (russian thistle), Sida spp. (sida), Sinapis arvensis (wild mustard), and Xanthium spp. (cocklebur).

Again where the exogenous chemical substance is glyphosate, annual narrowleaf species on which the method and compositions of the invention can be employed include, without limitation, Avena fatua (wild oat), Axonopus spp. (carpetgrass), Bromus tectorum (downy brome), Digitaria spp. (crabgrass), Echinochloa crus-galli (barnyardgrass), Eleusine indica (goosegrass), Lolium multiflorum (annual ryegrass), Oryza sativa (rice), Ottochioa nodosa (ottochloa), Paspalum notatum (bahiagrass), Phalaris spp. (canarygrass), Setaria spp. (foxtail), Triticum aestivum (wheat) and Zea mays (corn or maize).

Again where the exogenous chemical substance is glyphosate, perennial broadleaf species on which the method and compositions of the invention can be employed include, without limitation, Artemisia spp. (mugwort), Asclepias spp. (milkweed), Cirsium arvense (canada thistle), Convolvulus arvensis (field bindweed) and Pueraria spp. (kudzu).

Again where the exogenous chemical substance is glyphosate, perennial narrowleaf species on which the method and compositions of the invention can be employed include, without limitation, Brachiaria spp. (brachiaria), Cynodon dactylon (bermudagrass), Cyperus esculentus (yellow nutsedge), Cyperus rotundus (purple nutsedge), Elymus repens (quackgrass or couch), Imperata cylindrica (cogongrass or lalang), Lolium perenne (perennial ryegrass), Panicum maximum (guineagrass), Paspalum dilatatum (dallisgrass), Phragmites spp. (reed), Sorghum halepense (johnsongrass) and Typha spp. (cattail).

Again where the exogenous chemical substance is glyphosate, other perennial species not listed above on which the method and compositions of the invention can be employed include, without limitation, Equisetum spp. (horsetail), Pteridium aquilinum (bracken), Rubus spp. (blackberry) and Ulex europaeus (gorse).

Among systemic foliar-applied exogenous chemical substances, those which are water-soluble are particularly favored for use according to the present invention. More preferred among those are water-soluble salts comprising a biologically active ion and a counterion which has less or no biological activity. Even more preferred among such salts are those having a molecular weight, excluding counterions, of less than about 300. Especially preferred are those having one or more functional groups selected from amine, amide, carboxylate, phosphonate and phosphinate groups.

Among such especially preferred exogenous chemical substances are herbicides, for example glyphosate and glufosinate, plant growth regulators, for example ethephon, and nematicides, for example those disclosed in U.S Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

An anthraquinone compound is particularly useful in the method and compositions of the invention at rates from about 0.25 to about 250 g/ha, preferably from about 1 to about 25 g/ha, provided such rates are insufficient to antagonize effectiveness of the exogenous chemical substance. Anthraquinone compounds can be antagonistic to glyphosate if used for example at a rate of 50 g/ha or higher. When an anthraquinone compound is coformulated with glyphosate, the weight/weight ratio of anthraquinone compound to glyphosate acid equivalent is preferably in the range from about 1:500 to about 1:5, for example in the range from about 1:200 to about 1:10.

Such low ratios of anthraquinone compound to exogenous chemical substance mean that the anthraquinone compound can generally be included in a concentrate formulation while still enjoying the benefits of very high loading of active ingredient (i.e. exogenous chemical substance) in the concentrate formulation. For example, in the case of an aqueous solution or emulsion concentrate formulation of a water-soluble glyphosate salt such as the isopropylamine or trimethylsulfonium salt, a useful amount, for example from about 1 to about 5 g/l, of an anthraquinone compound can be included in the presence of a high concentration, for example from about 350 to about 500 g a.e./l, of glyphosate. Especially high loadings of glyphosate, for example from about 450 to about 500 g a.e./l, in an aqueous solution or emulsion concentrate formulation are often achievable only when the amount of surfactant in the formulation is reduced below the levels normally associated with consistent, reliable herbicidal performance; it is in this very situation where particularly great benefits can be obtained by including a small amount of an anthraquinone compound.

EXAMPLES

The glyphosate herbicidal efficacy enhancing properties of enhancing agents of the anthraquinone class were evaluated using a High Throughput Screening (HTS) protocol. In effect, the HTS screen measures the amount of regrowth experienced by barley plants that have been treated with a herbicidal formulation and subsequently clipped back to a height one centimeter above soil level. The actual procedures of the HTS screen are described below.

Three to five barley seeds are placed in a 50 mm square pot containing a growth medium of 50% Metro-Mix 350, 25% SA1 sand and 25% Bacto Mix. Additionally, Osmocote® fertilizer is applied at a rate of 3.53 kg/m$^3$. The pots are watered by sub-irrigation for the entire test period. Shortly after emergence, the pots are hand trimmed to two plants per pot. Greenhouse conditions consisting of a day/night temperature range of 29° C./21° C. with a 12 to 14 hour photoperiod are employed.

When the barley is approximately five inches to 12–15 cm tall, which is generally eight to nine days after planting, the plants are treated with the desired chemical formulation. Applications are performed using a track sprayer fitted either with an 8001E flat fan nozzle operating at a pressure of 172 kPa or with a 9501E flat fan nozzle operating at a pressure of 166 kPa. The spray volume is equivalent to 187 liters per hectare (l/ha). The treated plants are returned to the greenhouse. Forty-eight hours after treatment, all plants including those chemically treated and those that are untreated are clipped to a height of one centimeter above soil level.

Six pots containing two plants each are used to evaluate the effects of each treatment. Three days after the plants have been clipped, the plants are quantitatively measured for regrowth of the barley. Regrowth of the barley is measured from the point where the barley was clipped to the tip of the new growth. Each plant is measured separately. The recorded height of the treatment is the average height of the twelve individual plants. If desired, statistical analysis is performed using analysis of variance (ANOVA) at the 95% confidence level.

Chemical treatments illustrative of the present invention were made using dilute aqueous compositions. The aqueous compositions were generally prepared by dispersing solutions of the enhancing agents into water. The solutions of the enhancing agents were typically prepared by dissolving the enhancing agents into a water dispersible solvent such as dimethylsulfoxide. Glyphosate was included as an active herbicidal ingredient in each of these dilute aqueous compositions in the form of Formulation C. Formulation C consists of 41% by weight of the monoisopropylammonium salt of glyphosate in aqueous solution with a coformulant (15% by weight) of a surfactant (MON 0818 of Monsanto Company) based upon a 15EO tallowamine polyethoxylate. In each instance, Formulation C was employed at a concentration calculated to give a desired glyphosate acid equivalent (a.e.) rate in grams per hectare (g a.e./ha). Enhancing agents were included to obtain particular yet varied rates, i.e., they were not incorporated as a set ratio to glyphosate that varied proportionately with the rate of glyphosate but rather were varied independently of the glyphosate rate. The rate of the enhancing agent in each instance is given in g/ha. Each experiment was performed using a particular glyphosate concentration and a particular enhancing agent at particular application rates.

Chemical treatments used for standard comparative purposes were made by dilution of Formulation C to obtain in one instance 112 g a.e./ha and in another instance 224 g a.e./ha. Throughout, comparative treatments of the former type will on occasion be indicated by "1X" while comparative treatments of the latter type will be indicated by "2X". The comparative examples contained no enhancing agent of the anthraquinone or substituted anthraquinone family. For the present examples, the regrowth height determined for any particular treatment is compared to the respective regrowth heights for the standardized comparative treatments, i.e., 1X and 2X, and an additional control in which neither enhancing agent nor glyphosate were applied to the plants.

Each of the aqueous compositions evaluated was similarly prepared. Appropriate amounts of Formulation C and the particular enhancing agent were diluted in aqueous solution to achieve the desired concentrations of glyphosate and enhancing agent.

The tests were performed by varying the type and amount of enhancing agent employed and the amount of herbicide. Variations in the enhancing agent were obtained by varying the functional R groups attached to the base structure. Thus, for each test, a single enhancing agent was employed, but the concentration of both glyphosate and enhancing agent was varied. The following Tables describe the particular anthraquinone compounds employed with each test. The compounds are designated with numbers, e.g., Compound 1.

TABLE 1

| Compound | $R_1$ | $R_2$ | $R_3$ | $R_4$ | $R_5$ | $R_6$ | $R_7$ | $R_8$ |
|---|---|---|---|---|---|---|---|---|
| 1 | —NHCH$_3$ | —H | —H | —H | —H | —H | —H | —H |
| 2 | —NH$_2$ | —CH$_3$ | —Br | —H | —H | —H | —H | —H |
| 3 | —NH$_2$ | —H | —H | —H | —H | —H | —H | —H |
| 4 | —Cl | —H | —H | —H | —H | —H | —H | —H |
| 5 | —NH$_2$ | —NH$_2$ | —H | —H | —H | —H | —H | —H |
| 6 | —NH$_2$ | —H | —NH$_2$ | —H | —H | —H | —H | —H |
| 7 | —NH$_2$ | —H | —H | —H | —NH$_2$ | —H | —H | —H |
| 8 | —Cl | —H | —H | —H | —H | —H | —H | —Cl |
| 9 | —OH | —H | —H | —H | —H | —H | —H | —OH |
| 10 | —H | —CH$_2$OH | —H | —H | —H | —H | —H | —H |
| 11 | —H | —NH$_2$ | —H | —H | —H | —H | —H | —H |
| 12 | —H | —CH$_2$CH$_3$ | —H | —H | —H | —H | —H | —H |
| 13 | —H | —CH$_3$ | —H | —H | —H | —H | —H | —H |
| 14 | —H | —C(CH$_3$)$_3$ | —H | —H | —H | —H | —H | —H |
| 15 | —H | —NH$_2$ | —H | —H | —H | —NH$_2$ | —H | —H |
| 16 | —H | —SO$_3^-$Na$^+$ | —H | —H | —H | —H | —H | —H |
| 17 | —H | —SO$_3^-$Na$^+$ | —H | —H | —H | —SO$_3^-$Na$^+$ | —H | —H |

Treatments and corresponding HTS results are given in Table 2.

TABLE 2

| Compound | Enhancing Agent Name | Glyphosate Rate (g a.e./ha) | Enhancing Agent Rate (g/ha) | Regrowth Height (mm) |
|---|---|---|---|---|
| | Control | 0 | 0 | 55 |
| | Standard 1X | 112 | 0 | 51 |
| | Standard 2X | 224 | 0 | 30 |
| 1 | 1-(methylamino)-anthraquinone | 112 | 50 | 46 |
| 1 | 1-(methylamino)-anthraquinone | 112 | 20 | 43 |
| 1 | 1 -(methylamino)-anthraquinone | 112 | 2 | 45 |
| | Control | 0 | 0 | 61 |
| | Standard 1X | 112 | 0 | 36 |
| | Standard 2X | 224 | 0 | 22 |
| 2 | 1-amino-4-bromo-2-methyl anthraquinone | 112 | 50 | 35 |
| 2 | 1-amino-4-bromo-2-methyl anthraquinone | 112 | 20 | 32 |
| 2 | 1-amino-4-bromo-2-methyl anthraquinone | 112 | 2 | 32 |
| | Control | 0 | 0 | 61 |
| | Standard 1X | 112 | 0 | 36 |
| | Standard 2X | 224 | 0 | 22 |
| 3 | 1-aminoanthraquinone | 112 | 50 | 30 |
| 3 | 1-aminoanthraquinone | 112 | 20 | 29 |
| 3 | 1-aminoanthraquinone | 112 | 2 | 39 |
| | Control | 0 | 0 | 55 |
| | Standard 1X | 112 | 0 | 51 |
| | Standard 2X | 224 | 0 | 30 |
| 4 | 1-chloroanthraquinone | 112 | 50 | 50 |
| 4 | 1-chloroanthraquinone | 112 | 20 | 52 |
| 4 | 1-chloroanthraquinone | 112 | 2 | 49 |
| | Control | 0 | 0 | 61 |
| | Standard 1X | 112 | 0 | 36 |
| | Standard 2X | 224 | 0 | 22 |
| 5 | 1,2-diaminoanthraquinone | 112 | 50 | 25 |
| 5 | 1,2-diaminoanthraquinone | 112 | 20 | 27 |
| 5 | 1,2-diaminoanthraquinone | 112 | 2 | 31 |
| | Control | 0 | 0 | 55 |
| | Standard 1X | 112 | 0 | 51 |
| | Standard 2X | 224 | 0 | 30 |
| 6 | 1,4-diaminoanthraquinone | 112 | 50 | 49 |
| 6 | 1,4-diaminoanthraquinone | 112 | 20 | 42 |
| 6 | 1,4-diaminoanthraquinone | 112 | 2 | 48 |
| | Control | 0 | 0 | 55 |
| | Standard 1X | 112 | 0 | 51 |
| | Standard 2X | 224 | 0 | 30 |
| 7 | 1,5-diaminoanthraquinone | 112 | 50 | 52 |
| 7 | 1,5-diaminoanthraquinone | 112 | 20 | 45 |
| 7 | 1,5-diaminoanthraquinone | 112 | 2 | 45 |
| | Control | 0 | 0 | 55 |
| | Standard 1X | 112 | 0 | 51 |
| | Standard 2X | 224 | 0 | 30 |
| 8 | 1,8 dichloroanthraquinone | 112 | 50 | 42 |
| 8 | 1,8 dichloroanthraquinone | 112 | 20 | 50 |
| 8 | 1,8 dichloroanthraquinone | 112 | 2 | 47 |
| | Control | 0 | 0 | 61 |
| | Standard 1X | 112 | 0 | 36 |
| | Standard 2X | 224 | 0 | 22 |
| 9 | 1,8 dihydroxyanthraquinone | 112 | 50 | 3 1 |
| 9 | 1,8 dihydroxyanthraquinone | 112 | 20 | 36 |
| 9 | 1,8 dihydroxyanthraquinone | 112 | 2 | 39 |
| | Control | 0 | 0 | 61 |
| | Standard 1X | 112 | 0 | 36 |
| | Standard 2X | 224 | 0 | 22 |
| 10 | 2-(hydroxymethyl) anthraquinone | 112 | 50 | 28 |
| 10 | 2-(hydroxymethyl) anthraquinone | 112 | 20 | 28 |
| 10 | 2-(hydroxymethyl) anthraquinone | 112 | 2 | 24 |
| | Control | 0 | 0 | 55 |
| | Standard 1X | 112 | 0 | 51 |
| | Standard 2X | 224 | 0 | 30 |
| 11 | 2-aminoanthraquinone | 112 | 50 | 51 |
| 11 | 2-aminoanthraquinone | 112 | 20 | 48 |
| 11 | 2-aminoanthraquinone | 112 | 2 | 54 |
| | Control | 0 | 0 | 61 |
| | Standard 1X | 112 | 0 | 36 |
| | Standard 2X | 224 | 0 | 22 |
| 12 | 2-ethylanthraquinone | 112 | 50 | 35 |
| 12 | 2-ethylanthraquinone | 112 | 20 | 31 |

TABLE 2-continued

| Compound | Enhancing Agent Name | Glyphosate Rate (g a.e./ha) | Enhancing Agent Rate (g/ha) | Regrowth Height (mm) |
|---|---|---|---|---|
| 12 | 2-ethylanthraquinone | 112 | 2 | 35 |
|  | Control | 0 | 0 | 61 |
|  | Standard 1X | 112 | 0 | 36 |
|  | Standard 2X | 224 | 0 | 22 |
| 13 | 2-methylanthraquinone | 112 | 50 | 30 |
| 13 | 2-methylanthraquinone | 112 | 20 | 25 |
| 13 | 2-methylanthraquinone | 112 | 2 | 29 |
|  | Control | 0 | 0 | 61 |
|  | Standard 1X | 112 | 0 | 36 |
|  | Standard 2X | 224 | 0 | 22 |
| 14 | 2-tert-butylanthraquinone | 112 | 50 | 34 |
| 14 | 2-tert-butylanthraquinone | 112 | 20 | 33 |
| 14 | 2-tert-butylanthraquinone | 112 | 2 | 64 |
|  | Control | 0 | 0 | 61 |
|  | Standard 1X | 112 | 0 | 36 |
|  | Standard 2X | 224 | 0 | 22 |
| 15 | 2,6-diaminoanthraquinone | 112 | 50 | 27 |
| 15 | 2,6-diaminoanthraquinone | 112 | 20 | 31 |
| 15 | 2,6-diaminoanthraquinone | 112 | 2 | 32 |
|  | Control | 0 | 0 | 61 |
|  | Standard 1X | 112 | 0 | 36 |
|  | Standard 2X | 224 | 0 | 22 |
| 16 | anthraquinone-2-sulfonic acid, sodium salt monohydrate | 112 | 50 | 52 |
| 16 | anthraquinone-2-sulfonic acid, sodium salt monohydrate | 112 | 20 | 44 |
| 16 | anthraquinone-2-sulfonic acid, sodium salt monohydrate | 112 | 2 | 29 |
|  | Control | 0 | 0 | 63 |
|  | Standard 1X | 112 | 0 | 29 |
|  | Standard 2X | 224 | 0 | 21 |
| 17 | anthraquinone-2,6-disulfonic acid, disodium salt | 112 | 50 | 53 |
| 17 | anthraquinone-2,6-disulfonic acid, disodium salt | 112 | 20 | 50 |
| 17 | anthraquinone-2,6-disulfonic acid, disodium salt | 112 | 2 | 32 |

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for treating a plant with glyphosate comprising the steps of:
   (a) applying to foliage of the plant an anthraquinone compound; and
   (b) applying a biologically effective amount of said glyphosate to the same foliage; wherein:
   said anthraquinone compound is applied in a substantially non-phytotoxic amount of at least about 0.25 g/ha but not sufficient to antagonize effectiveness of said glyphosate;
   said glyphosate is N-phosphonomethylglycine, a salt of N-phosphonomethylglycine, an ester of N-phosphonomethylglycine, a compound which is converted to N-phosphonomethylglycine in plant tissues, or a compound which otherwise provides N-phosphonomethylglycine in ionic form; and
   the biological effect on a plant treated with said anthraquinone compound and said glyphosate is greater than the biological effect on a plant treated with said glyphosate but without said anthraquinone compound.

2. The process of claim 1 wherein step (b) occurs within 24 hours before or after step (a).

3. The process of claim 2 wherein step (b) occurs within 24 hours after step (a).

4. The process of claim 1 wherein steps (a) and (b) occur simultaneously and said anthraquinone compound and said glyphosate are applied by spraying a single spray composition containing said anthraquinone compound and said glyphosate.

5. The process of claim 4 which further comprises, prior to steps (a) and (b), a step of mixing said anthraquinone compound and said glyphosate with suitable formulation ingredients to form a concentrate composition, and a step of diluting, dissolving or dispersing said concentrate composition in water to form the spray composition.

6. The process of claim 4 wherein the spray composition further comprises a surfactant.

7. The process of claim 4 wherein said glyphosate is a water-soluble salt of N-phosphonomethylglycine.

8. The process of claim 7 wherein the salt is an alkali metal, ammonium, alkylamine, alkanolamine or alkylsulfonium salt.

9. The process of claim 1 wherein said glyphosate is an alkali metal N-phosphonomethylglycine salt, an ammonium N-phosphonomethylglycine salt, an alkylamine N-phosphonomethylglycine salt, an alkanolamine N-phosphonomethylglycine salt, or an alkylsulfonium N-phosphonomethylglycine salt.

10. The process of claim 1 wherein said anthraquinone compound has the formula:

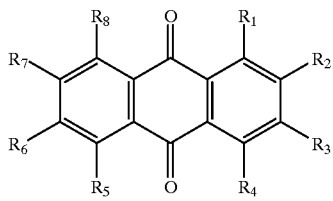

where $R_1$ through $R_4$ and $R_5$ through $R_8$ are independently hydrogen, alkyl groups having from 1 to 30 carbon atoms, alkenyl groups having from 2 to 30 carbon atoms, alkoxy groups having from 1 to 30 carbon atoms, halogen, amino groups, alkylamino groups having from 1 to 30 carbon atoms, hydroxy groups, hydroxyalkyl groups having from 1 to 30 carbon atoms, cyano groups, nitro groups, haloalkyl groups having from 1 to 30 carbon atoms, carboxy groups, and aryl groups having 1 to 30 carbon atoms.

11. The process of claim 10 wherein $R_1$ is hydrogen, —$NH_2$, or —$NHCH_3$; $R_2$ is hydrogen, hydroxymethyl, methyl, or —$NH_2$; $R_5$ and $R_6$ are independently hydrogen or —$NH_2$; and $R_3$, $R_4$, $R_7$, and $R_8$ are hydrogen.

12. The process of claim 10 wherein one or two of $R_1$, $R_2$, $R_3$, $R_4$, $R_5$, $R_6$, $R_7$, and $R_8$ are independently methyl, ethyl, hydroxymethyl, amino, or methylamino and all other R substituents are hydrogen.

13. The process of claim 10 wherein the anthraquinone compound is applied at a rate of from about 0.25 to about 250 g/ha.

14. The process of claim 10 wherein the anthraquinone compound is applied at a rate of from about 1 to about 25 g/ha.

15. The process of claim 1 wherein said glyphosate is water-soluble.

16. The process of claim 15 wherein the exogenous chemical composition is a salt comprising a biologically active ion and a counterion which has less or no biological activity.

17. A herbicidal process comprising the steps of:
(a) mixing together (i) an anthraquinone compound in an amount sufficient to provide a rate of from about 1 to about 25 g/ha, (ii) a herbicidally effective amount of a glyphosate selected from the group consisting of an alkali metal N-phosphonomethylglycine salt, an ammonium N-phosphonomethylglycine salt, an alkylamine N-phosphonomethylglycine salt, an alkanolamine N-phosphonomethylglycine salt, and an alkylsulfonium N-phosphonomethlglycine salt, (iii) one or more surfactants in a total surfactant amount sufficient to emulsify the anthraquinone compound and to enhance the herbicidal effectiveness of the N-phosphonomethylglycine, and (iv) water to form a concentrate;
(b) diluting the concentrate in water to form a spray composition; and
(c) spraying the spray composition on foliage of plants in a field; wherein the herbicidal effect on foliage treated with said anthraquinone compound and said glyphosate is greater than the herbicidal effect on foliage treated with said glyphosate but without said anthraquinone compound.

18. A plant treatment composition comprising glyphosate and an anthraquinone compound; wherein:
when the composition is applied to foliage of a plant with or without prior dilution, dispersion or dissolution in an application medium, the exogenous chemical substance is in a biologically effective amount and said anthraquinone compound is in a substantially non-phytotoxic amount of at least about 0.25 g/ha but not sufficient to antagonize effectiveness of said glyphosate; and
said glyphosate is N-phosphonomethylglycine, a salt of N-phosphonomethylglycine, an ester of N-phosphonomethylglycine, a compound which is converted to N-phosphonomethylglycine in plant tissues, or a compound which otherwise provides N-phosphonomethlglycine in ionic form.

19. The composition of claim 18 wherein said anthraquinone compound has the formula:

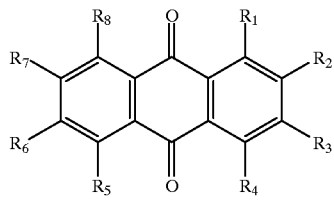

where $R_1$ through $R_4$ and $R_5$ through $R_8$ are independently hydrogen, alkyl groups having from 1 to 30 carbon atoms, alkenyl groups having from 2 to 30 carbon atoms, alkoxy groups having from 1 to 30 carbon atoms, halogen, amino groups, alkylamino groups having from 1 to 30 carbon atoms, hydroxy groups, hydroxyalkyl groups having from 1 to 30 carbon atoms, cyano groups, nitro groups, haloalkyl groups having from 1 to 30 carbon atoms, carboxy groups, and aryl groups having 1 to 30 carbon atoms.

20. The composition of claim 19 wherein $R_1$ is hydrogen, —$NH_2$, or —$NHCH_3$; $R_2$ is hydrogen, hydroxymethyl, methyl, or —$NH_2$; $R_5$ and $R_6$ are independently hydrogen or —$NH_2$; and $R_3$, $R_4$, $R_7$, and $R_8$ are hydrogen.

21. The composition of claim 19 wherein one or two of $R_1$, $R_2$, $R_3$, $R_4$, $R_5$, $R_6$, $R_7$, and $R_8$ are independently methyl, ethyl, hydroxymethyl, amino, or methylamino and all other R substituents are hydrogen.

22. The composition of claim 18 wherein said glyphosate is water-soluble.

23. The composition of claim 22 wherein said glyphosate is a salt comprising a biologically active ion and a counterion which has less or no biological activity.

24. The composition of claim 18 wherein said glyphosate is an alkali metal N-phosphonomethylglycine salt, an ammonium N-phosphonomethylglycine salt, an alkylamine N-phosphonomethylglycine salt, an alkanolamine N-phosphonomethylglycine salt, or an alkylsulfonium N-phosphonomethylglycine salt.

25. The composition of claim 18 which is an aqueous solution or emulsion concentrate formulation wherein the N-phosphonomethylglycine is present in a concentration of from about 50 to about 500 g a.e./l.

26. The composition of claim 25 wherein the N-phosphonomethylglycine is present in a concentration of from about 350 to about 500 g a.e./l.

27. The composition of claim 25 wherein the N-phosphonomethylglycine is present in a concentration of from about 450 to about 500 g a.e./l.

28. The composition of claim 25 which is an emulsion having an aqueous phase and an oil phase, wherein the N-phosphonomethylglycine is present primarily in the aqueous phase and the anthraquinone compound is present primarily in the oil phase.

29. The composition of claim 18 which is a water-soluble or water-dispersible dry formulation wherein the N-phosphonomethylglycine is present in a concentration of from about 5% to about 80% a.e. by weight.

30. The composition of claim 29 wherein the N-phosphonomethylglycine is present in a concentration of from about 50% to about 80% a.e. by weight.

31. The composition of claim 18 which further comprises one or more surfactants.

32. The composition of claim 31 wherein at least one of the surfactants is nonionic, cationic or amphoteric.

33. The composition of claim 32 wherein at least one of the surfactants is a nonionic surfactant selected from the group consisting of polyoxyalkylene alkyl and alkylaryl ethers, polyoxyalkylene alkyl esters, sorbitan alkyl esters, glyceryl alkyl esters, sucrose esters and alkyl polyglycosides.

34. The composition of claim 32 wherein at least one of the surfactants is a cationic surfactant selected from the group consisting of polyoxyalkylene tertiary alkylamines, quaternary ammonium surfactants and polyoxyalkylene alkyletheramines.

35. The composition of claim 32 wherein at least one of the surfactants is an amphoteric surfactant selected from the group consisting of polyoxyalkylene alkylamine oxides, alkylbetaines and alkyl-substituted amino acids.

36. The composition of claim 18 wherein the anthraquinone compound is present in an amount such that when the composition is applied by spraying, the anthraquinone compound is applied at a rate of from about 0.25 to about 250 g/ha.

37. The composition of claim 18 wherein the anthraquinone compound is present in an amount such that when the composition is applied by spraying, the anthraquinone compound is applied at a rate of from about 1 to about 25 g/ha.

38. A concentrate herbicidal composition comprising (i) from about 1 to about 5 g/l of an anthraquinone compound, (ii) from about 350 to about 500 g a.e./l of an N-phosphonomethylglycine salt selected from the group consisting of an alkali metal N-phosnhonomethlglycine salt, an ammonium N-phosphonomethylglcine salt, an alkylamine N-phosphonomethlglycine salt, an alkanolamine N-phosphonomethlglycine salt and an alkylsulfonium N-phosphonomethylglycine salt, (iii) one or more surfactants in a total surfactant amount sufficient to emulsify the anthraquinone compound, and (iv) water.

39. The composition of claim 38 comprising from about 450 to about 500 g a.e./l of the N-phosphonomethylglycine salt.

40. The composition of claim 38 wherein at least one of the surfactants is a cationic surfactant selected from the group consisting of polyoxyalkylene tertiary alkylamines, quaternary ammonium surfactants and polyoxyalkylene alkyletheramines.

* * * * *